United States Patent [19]

Blair et al.

[11] Patent Number: 5,817,703
[45] Date of Patent: Oct. 6, 1998

[54] REBOND FOAM AND PROCESS FOR PRODUCTION THEREOF

[75] Inventors: G. Ronald Blair, Richmond Hill; Harold R. Attfield, Etobicoke, both of Canada; Robert N. Wilson, Hixson, Tenn.

[73] Assignee: Woodbridge Foam Corporation, Canada

[21] Appl. No.: 723,308

[22] Filed: Sep. 30, 1996

[51] Int. Cl.$^6$ .................................................. C08J 9/236
[52] U.S. Cl. .............................. 521/53; 521/54; 521/59; 521/137; 604/358; 604/369
[58] Field of Search ........................... 521/54, 59, 137, 521/53; 604/358, 369

[56] References Cited

U.S. PATENT DOCUMENTS

| | | | |
|---|---|---|---|
| 3,171,820 | 3/1965 | Volz | 260/2.5 |
| 3,175,025 | 3/1965 | Geen et al. | 264/80 |
| 3,781,231 | 12/1973 | Janssen et al. | 260/2.5 BE |
| 3,799,898 | 3/1974 | Lamplugh et al. | 260/2.5 AD |
| 3,900,030 | 8/1975 | Bashan | 128/285 |
| 4,062,817 | 12/1977 | Westerman | 260/17.45 G |
| 4,066,583 | 1/1978 | Spaulding | 260/17.4 SG |
| 4,167,464 | 9/1979 | George | 204/159.23 |
| 4,190,562 | 2/1980 | Westerman | 260/17.4 UC |
| 4,259,452 | 3/1981 | Yukuta et al. | 521/914 |
| 4,394,930 | 7/1983 | Korpman | 220/444 |
| 4,466,993 | 8/1984 | Hou et al. | 427/44 |
| 4,486,489 | 12/1984 | George | 428/220 |
| 4,699,619 | 10/1987 | Bernardin | 604/378 |
| 4,715,918 | 12/1987 | Lang | 156/273.1 |
| 4,725,629 | 2/1988 | Garvey et al. | 521/137 |
| 4,731,391 | 3/1988 | Garvey | 521/137 |
| 4,775,375 | 10/1988 | Aledo | 604/378 |
| 4,798,876 | 1/1989 | Gould et al. | 525/457 |
| 4,810,582 | 3/1989 | Gould et al. | 428/423.1 |
| 4,960,477 | 10/1990 | Mesek | 156/209 |
| 4,977,892 | 12/1990 | Ewall | 128/156 |
| 4,985,467 | 1/1991 | Kelly et al. | 521/52 |
| 5,009,650 | 4/1991 | Bernardin | 604/378 |
| 5,098,423 | 3/1992 | Pieniak et al. | 604/385.1 |
| 5,176,668 | 1/1993 | Bernardin | 604/368 |
| 5,185,009 | 2/1993 | Sitnam | 604/364 |
| 5,188,624 | 2/1993 | Young, Sr. et al. | 604/378 |
| 5,188,626 | 2/1993 | Toyoda et al. | 604/385.1 |
| 5,219,342 | 6/1993 | Hatch et al. | 604/386.1 |
| 5,246,431 | 9/1993 | Minetola et al. | 604/385.2 |
| 5,257,982 | 11/1993 | Cohen et al. | 604/378 |
| 5,261,900 | 11/1993 | Houle et al. | 604/385.1 |
| 5,263,948 | 11/1993 | Karami et al. | 604/383 |
| 5,263,949 | 11/1993 | Karami et al. | 604/383 |
| 5,275,590 | 1/1994 | Huffman et al. | 604/385.2 |
| 5,300,054 | 4/1994 | Feist et al. | 604/378 |
| 5,304,161 | 4/1994 | Noel et al. | 604/378 |
| 5,328,935 | 7/1994 | Van Phan et al. | 521/150 |
| 5,330,457 | 7/1994 | Cohen | 604/378 |
| 5,334,177 | 8/1994 | Cohen | 604/378 |
| 5,336,695 | 8/1994 | Nass et al. | 521/137 |
| 5,338,766 | 8/1994 | Phan et al. | 521/149 |
| 5,342,344 | 8/1994 | Lancaster et al. | 604/387 |
| 5,350,776 | 9/1994 | Raad | 521/54 |
| 5,370,634 | 12/1994 | Ando et al. | 604/385.1 |
| 5,401,266 | 3/1995 | Runeman et al. | 604/378 |
| 5,439,458 | 8/1995 | Noel et al. | 604/378 |
| 5,447,508 | 9/1995 | Numano et al. | 604/385.2 |
| 5,451,613 | 9/1995 | Smith | 521/54 |
| 5,462,541 | 10/1995 | Bruemmer et al. | 604/391 |
| 5,486,167 | 1/1996 | Dragoo et al. | 604/384 |
| 5,531,727 | 7/1996 | Cohen et al. | 604/378 |
| 5,674,917 | 10/1997 | Wilson | 521/137 |
| 5,719,201 | 2/1998 | Wilson | 521/137 |

FOREIGN PATENT DOCUMENTS

| | | | |
|---|---|---|---|
| 1207486 | 7/1986 | Canada | C08L 75/04 |
| 1250190 | 2/1989 | Canada | C09J 7/02 |
| 0288865 | 11/1991 | European Pat. Off. | |
| 4233289 | 4/1994 | Germany | C08L 75/04 |
| 4308347 | 9/1994 | Germany | C08L 75/04 |
| 5792032 | 6/1982 | Japan | C08J 9/02 |
| 1317930 | 5/1973 | United Kingdom | C08G 22/44 |
| 1354576 | 5/1974 | United Kingdom | C08G 22/46 |

OTHER PUBLICATIONS

"Urethane Chemicals Preliminary Data Sheet", Olin Urethane Chemical.
"Scott Acquell Foam", Foam Division, Scott Paper Co.

Primary Examiner—Morton Foelak
Attorney, Agent, or Firm—Fitzpatrick, Cella, Harper & Scinto

[57] ABSTRACT

A rebond foam comprising a plurality of isocyanate-based polymeric foam pieces bonded to one another with an isocyanate-based binder is disclosed. A superabsorbent material is comprised in one or both of the isocyanate-based polymeric foam pieces and the isocyanate-based binder. The rebond foam is capable of: (i) absorbing at least about 5 times its weight of a 0.9 wt./wt. % aqueous NaCl solution maintained at a temperature of from about 20° to about 25° C., and (ii) retaining at least about 5 times its weight of absorbed aqueous NaCl solution which is bound to the superabsorbent material. A process for producing a rebond foam is also disclosed. The process comprises the steps of: (i) mixing a plurality of isocyanate-based foam pieces with a binder comprising an isocyanate and an active hydrogen-containing compounds to form a mixture, a superabsorbent material being comprised in one or both of the isocyanate-based polymeric foam pieces and the isocyanate-based binder; (ii) placing the mixture in a mold; (iii) compressing the mixture in the mold; (iv) reacting the isocyanate and the active hydrogen-containing compound; (v) bonding the isocyanate-based foam pieces to one another to form the rebond foam. The rebond foam is useful as applications where fluid absorption and retention is desirable (e.g. personal hygiene devices, etc.).

22 Claims, No Drawings

5,817,703

REBOND FOAM AND PROCESS FOR PRODUCTION THEREOF

BACKGROUND OF THE INVENTION

1. Field of the Invention

The present invention relates to a rebond foam and to a process for production thereof.

2. Description of the Prior Art

Rebond foam is known in the art of isocyanate-based polymeric foams. Specifically, it is known to mix pieces of foam with a binder which serves to bond the pieces to one another. Rebonding technology has been used for a number of years to recycle, inter alia, polyurethane foams. Generally, the rebonded polyurethane foam product has been used in carpet underlayment pad, and specific seating and cushioning applications. Given the prior applications for rebond foam, it is not surprising that these foams are typically not used in applications where fluid absorption is desirable.

Foamed isocyanate-based polymers containing superabsorbent materials are known. A particularly preferred class of such foam isocyanate-based polymers is taught in copending United States patent application Ser. No. 08/413,433 (Wilson; filed Mar. 30, 1995), Ser. No. 08/554,896 (Wilson; filed Nov. 9, 1995), Ser. No. 08/674,242 (Wilson; filed Jul. 1, 1996) and Ser. No. 08/674,190 (Wilson et al; filed Jul. 1, 1996), collectively referred to as "the Wilson applications", the contents of each of which are hereby incorporated by reference.

While the foamed isocyanate-based polymers described in the Wilson applications represent a significant advance in the art, it would be desirable to have a means to recycle

SUMMARY OF THE INVENTION

It is an object of the present invention to provide a novel rebond foam.

It is another object of the present invention to provide a novel process for producing a rebond foam.

Accordingly, in one of its aspects, the present invention provides a rebond foam comprising a plurality of isocyanate-based polymeric foam pieces bonded to one another with an isocyanate-based binder, a superabsorbent material being comprised in one or both of the isocyanate-based polymeric foam pieces and the isocyanate-based binder, the rebond foam being capable of: (i) absorbing at least about 5 times its weight of a 0.9 wt./wt. % aqueous NaCl solution maintained at a temperature of from about 20° to about 25° C., and (ii) retaining at least about 5 times its weight of absorbed aqueous NaCl solution which is bound to the superabsorbent material.

In another of its aspects, the present invention provides a process for producing a rebond foam comprising the steps of:

(i) mixing a plurality of isocyanate-based foam pieces with a binder comprising an isocyanate and an active hydrogen-containing compounds to form a mixture, a superabsorbent material being comprised in one or both of the isocyanate-based polymeric foam pieces and the isocyanate-based binder;

(ii) placing the mixture in a mold;

(iii) compressing the mixture in the mold;

(iv) reacting the isocyanate and the active hydrogen-containing compound;

(v) bonding the isocyanate-based foam pieces to one another to form the rebond foam.

As used throughout this specification, the term "rebond foam" is intended to mean a foam comprising a plurality of foam pieces which have been bonded together with a binder to produce an integral body. Further, as used throughout this specification, the term "isocyanate-based polymeric foam" is intended to mean, inter alia, polyurethane foam, polyurea foam and polyisocyanurate foam. Still further, as used throughout this specification, the term superabsorbent material is intended to mean a compound which is capable of absorbing at least about 10 times its weight of a 0.9 wt./wt. % aqueous NaCl solution maintained at a temperature in the range of from about 20° to about 25° C.

Thus, the present inventors have surprisingly and unexpectedly discovered that, contrary to conventional wisdom, a useful rebond foam can be made when one or both of the isocyanate-based polymeric foam pieces and the isocyanate-based binder contain a superabsorbent material Specifically, it has been discovered that, notwithstanding the process used to produce the rebond foam, the resulting rebond foam possesses absorption and retention properties (discussed in more detail hereinbelow) close to a virgin foam containing the same superabsorbent material at the same loading level.

The present rebond foam is comprised isocyanate-based polymeric foam pieces bonded to one another with an isocyanate-based binder. Preferably, both the present rebond foam is comprised of polyurethane foam pieces bonded to one another with a polyurethane binder. In this regard, it is possible that one or both of the polyurethane foam pieces and the polyurethane binder are based on an isocyanate and a polyol, wherein the polyol may be a single polyol or a mixture of polyols which possesses an overall ethylene oxide content in the range of from about 15 to about 80, preferably from about 20 to about 70, more preferably from about 35 to about 70, most preferably from about 50 to about 65, percent by weight, the remainder comprised of other polyoxyalkylene groups such as propylene oxide, butylene oxide or mixtures thereof.

While applications for present rebond material will be immediately apparent to those of skill in the art, it is believed that the rebond material is particularly useful in personal hygiene devices such as disposable diapers, disposable training pants, sanitary napkins, incontinence pads, bandage gauze and the like.

DETAILED DESCRIPTION OF THE PREFERRED EMBODIMENTS

Thus, Step (i) in the present process comprises mixing a plurality of isocyanate-based foam pieces with a binder comprising an isocyanate and an active hydrogen-containing compounds to form a mixture, a superabsorbent material being comprised in one or both of the isocyanate-based polymeric foam pieces and the isocyanate-based binder.

The superabsorbent material may be comprised in the foam pieces (this is preferred), the binder or both.

Generally, the isocyanate-based polymeric foam pieces may be selected from the group consisting of polyurethane foam, polyurea foam, polyisocyanurate foam, urea-modified polyurethane foam, urethane-modified polyurea foam, urethane-modified polyisocyanurate foam and urea-modified polyisocyanurate foam. The preferred isocyanate-based polymeric foam pieces may be selected from the group consisting of polyurethane foam and urea-modified polyurethane foam. The most preferred isocyanate-based polymeric foam pieces are polyurethane foam. As is known in the art, the term "modified", when used in conjunction with a polyurethane, polyurea or polyisocyanurate means that up to 50% of the polymer backbone forming linkages have been substituted.

The isocyanate-based polymeric foam pieces (also referred to as "the foam pieces) may be obtained from a foam body using any conventional technique. For example, the foam pieces may be obtained by shredding, comminuting or otherwise tearing the foam body into relatively small pieces. The size of the foam pieces is not particularly restricted provided that the foam pieces are: (i) not too small such that excessive amounts of binder will be needed and/or the cellular structure of the foam pieces is lost, and (ii) not too large such that handling thereof in the process is difficult. Generally, it is preferred that the foam pieces have a diameter in the range of from about 0.2 to about 1.0 inches, more preferably from about 0.2 to about 0.8 inches. In this context, "diameter" is intended to have a broad meaning and includes the longest distance passing substantially through the center of the foam piece.

If the foam pieces do not comprise the superabsorbent material, they may be regarded as conventional isocyanate-based polymeric foams. The production of such foams is conventional in the art—see, for example, "FLEXIBLE POLYURETHANE FOAMS" by Herrington et al. (1991), the contents of which are incorporated herein by reference.

A particularly preferred class of foam pieces for use herein are derived from an isocyanate-based polymeric foam containing a superabsorbent material Such a foam is taught in the Wilson applications referred to hereinabove and incorporated herein by reference.

The foam pieces (with or without superabsorbent material incorporated therein) used in the present process are based on an isocyanate. The isocyanate suitable for use is not particularly restricted and the choice thereof is within the purview of a person skilled in the art. Generally, the isocyanate compound suitable for use may be represented by the general formula:

$$Q(NCO)_i$$

wherein i is an integer of two or more and Q is an organic radical having the valence of i. Q may be a substituted or unsubstituted hydrocarbon group (e.g. an alkylene or arylene group). Moreover, Q may be represented by the general formula:

$$Q^1-Z-Q^1$$

wherein $Q^1$ is an alkylene or arylene group and Z is chosen from the group comprising —O—, —O—$Q^1$, —CO—, —S—, —S—$Q^1$—S— and —SO$_2$—. Examples of isocyanate compounds which fall within the scope of this definition include hexamethylene diisocyanate, 1,8-diisocyanato-p-methane, xylyl diisocyanate, (OCNCH$_2$CH$_2$CH$_2$OCH$_2$O)$_2$, 1-methyl-2,4-diisocyanatocyclohexane, phenylene diisocyanates, toluene diisocyanates, chlorophenylene diisocyanates, diphenylmethane-4,4'-diisocyanate, naphthalene-1,5-diisocyanate, triphenyl-methane-4,4',4'-triisocyanate and isopropylbenzene-alpha-4-diisocyanate.

In another embodiment, Q may also represent a polyurethane radical having a valence of i. In this case Q(NCO)$_i$ is a compound which is commonly referred to in the art as a prepolymer. Generally, a prepolymer may be prepared by reacting a stoichiometric excess of an isocyanate compound (as defined hereinabove) with an active hydrogen-containing compound (as defined hereinafter), preferably the polyhydroxyl-containing materials or polyols described below. In this embodiment, the polyisocyanate may be, for example, used in proportions of from about 30 percent to about 200 percent stoichiometric excess with respect to the proportion of hydroxyl in the polyol The prepolymer may then be reacted with a polyol, aqueous blowing agent (water), catalyst and, optionally, other additives, to produce a polyurethane foam or an amine to produce a polyurea-modified polyurethane.

In another embodiment, the isocyanate compound suitable for use in producing the foam pieces may be selected from dimers and trimers of isocyanates and diisocyanates, and from polymeric diisocyanates having the general formula:

$$[Q'(NCO)_i]_j$$

wherein both i and j are integers having a value of 2 or more, and Q' is a polyfunctional organic radical, and/or, as additional components in the reaction mixture, compounds having the general formula:

$$L(NCO)_i$$

wherein i is an integer having a value of 1 or more and L is a monofunctional or polyfunctional atom or radical. Examples of isocyanate compounds which fall with the scope of this definition include ethylphosphonic diisocyanate, phenylphosphonic diisocyanate, compounds which contain a =Si—NCO group, isocyanate compounds derived from sulfonamides (QSO$_2$NCO), cyanic acid and thiocyanic acid.

See also for example, British patent No. 1,453,258, the contents of which are incorporated herein by reference.

Non-limiting examples of suitable isocyanates include: 1,6-hexamethylene diisocyanate, 1,4-butylene diisocyanate, furfrylidene diisocyanate, 2,4-toluene diisocyanate, 2,6-toluene diisocyanate, 2,4'-diphenylmethane diisocyanate, 4,4'-diphenylmethane diisocyanate, 4,4'-diphenylpropane diisocyanate, 4,4'-diphenyl-3,3'-dimethyl methane diisocyanate, 1,5-naphthalene diisocyanate, 1-methyl-2,4-dissocyanate-5-chorobenzene, 2,4-diisocyanato-s-triazine, 1-methyl-2,4-diisocyanato cyclohexane, p-phenylene diisocyanate, m-phenylene diisocyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl-4-isocyanatophenyl)methane polymethylene polyphenyl polyisocyanates and mixtures thereof A more preferred isocyanate is selected from the group comprising 2,4-toluene diisocyanate, 2,6-toluene diisocyanate and mixtures thereof for example, a mixture comprising from about 75 to about 85 percent by weight 2,4-toluene diisocyanate and from about 15 to about 25 percent by weight 2,6-toluene diisocyanate. Another more preferred isocyanate is selected from the group comprising 2,4'-diphenylmethane diisocyanate, 4,4'-diphenylmethane diisocyanate and mixtures thereof. The most preferred isocyanate is a mixture comprising from about 15 to about 25 percent by weight 2,4'-diphenylmethane diisocyanate and from about 75 to about 85 percent by weight 4,4'-diphenylmethane diisocyanate. An example of such an isocyanate is commercially available from Imperial Chemical Industries under the tradename Rubinate M and from The Dow Chemical Company under the tradename PAPI 4027.

The foam pieces (with or without superabsorbent material incorporated therein) are produced by reacting an isocyanate as described hereinabove with an active hydrogen-containing compound. The active hydrogen-containing compound may be selected from the group consisting of hydrophilic hydrogen-containing compounds, non-hydrophilic hydrogen-containing compounds and mixtures thereof Preferably, the active hydrogen-containing compound comprises from about 10% to 100% by weight of a hydrophilic active hydrogen-containing compound and from 0 to about 90% by weight a non-hydrophilic active hydrogen-containing compound. More preferably, the active hydrogen-containing compound comprises from about 20% to about 90%, even more preferably from about 40% to about 90%, most preferably from about 60% to about 80%, by weight of a hydrophilic active hydrogen-containing compound and more preferably from about 10% to about 80%, even more preferably from about 10% to about 60%, most preferably from about 20% to about 30%, by weight a non-hydrophilic active hydrogen-containing compound.

Preferably, the hydrophilic active hydrogen-containing compound is a hydrophilic polyol. As is known in the art, the term "hydrophilic polyol" is intended to mean a polyol which confers hydrophilicity to the foam product. Ideally the hydrophilic polyol has a molecular weight in the range of from about 1500 to about 6000. Preferably, the hydrophilic polyol is selected from the group consisting of diols, triols, tetrols and mixtures thereof each of which contain polyoxyalkylene groups, the polyoxyalkylene groups comprising at least about 25, more preferably from about 40 to about 85, most preferably from about 55 to about 85, percent by weight of ethylene oxide. As is known in the art, the balance of the polyoxyalkylene groups is conventionally made up of one or both of propylene oxide and butylene oxide, preferably solely propylene oxide. A particularly preferred hydrophilic polyol is commercially available from The Dow Chemical Company under the tradename Voranol CP1421. Another preferred hydrophilic polyol is commercially available from Arco Chemical Company under the tradename Arcol 2580. Yet another preferred hydrophilic polyol is commercially available from BASF Corporation under the tradename Pluracol 593.

Alternatively, if it is desired to produce a polyurea, the active hydrogen-containing compound may be derived from a hydrophilic polyol as described above which as been reacted or capped with an amine. Such amination is within the purview of a person skilled in the art.

The non-hydrophilic active hydrogen-containing compound, if present, is selected from the group consisting of non-hydrophilic polyols, polyamines, polyamides, polyimines, polyolamines and mixtures thereof If the foam pieces are polyurethane foam, the non-hydrophilic active hydrogen-containing compound is typically a non-hydrophilic polyol. Generally, if such non-hydrophilic polyols contain or are based on ethylene oxide, the ethylene oxide will be present in amounts of less than about 20% by weight. The choice of such a polyol is not particularly restricted and is within the purview of a person skilled in the art. For example, the polyol may be a hydroxyl-terminated compound selected from the group comprising polyether, polyester, polycarbonate, polydiene and polycaprolactone. The polyol may be selected from the group comprising hydroxyl- terminated polyhydrocarbons, hydroxyl-terminated polyformals, fatty acid triglycerides, hydroxyl-terminated polyesters, hydroxymethyl-terminated polyesters, hydroxymethyl-terminated perfluoromethylenes, polyalkylene ether glycols, polyalklenearyleneether glycols and polyalkyleneether triols. The polyol may also be selected from the group comprising adipic acid-ethylene glycol polyester; poly(butylene glycol), poly(propylene glycol) and hydroxyl-terminated polybutadiene—see, for example, British patent No. 1,482,213, the contents of which are incorporated herein by reference. Preferably, such a polyol has a molecular weight in the range of from about 200 to about 10,000, more preferably from about 1,500 to about 4,300, most preferably from about 3,000 to about 4,100. Ideally, such a polyol would contain predominantly secondary hydroxyl groups.

As discussed above, it is possible to utilize a prepolymer technique to produce a polyurethane foam useful as the pieces in the present invention In one embodiment, it is contemplated that the prepolymer be prepared by reacting an excess of isocyanate with a hydrophilic polyol (as discussed above). The prepolymer could then be reacted with a non-hydrophilic polyol (as discussed above) to produce a polyurethane foam or an amine to produce a polyurea-modified polyurethane. In another embodiment, it is contemplated that the prepolymer be prepared by reacting an excess of isocyanate with a non-hydrophilic polyol (as discussed above). The prepolymer could then be reacted with a hydrophilic polyol (as discussed above) to produce a polyurethane foam. In yet another embodiment, if a single polyol provides a desirable overall ethylene oxide content (as discussed above), the same polyol can be used to prepare and react the prepolymer ultimately to produce a polyurethane foam. Another approach, when producing polyurethane foam, is to react an excess of the polyol (a mixture of hydrophilic and non-hydrophilic polyols or a single polyol which provides a desirable overall ethylene oxide content, both as discussed above) with an isocyanate to produce a prepolymer. The prepolymer could then be reacted with further isocyanate (the same as or different from the isocyanate used to prepare the prepolymer) to produce the polyurethane foam.

If the foam pieces are derived from a polyurea-modified polyurethane foam, the non-hydrophilic active hydrogen-containing compound comprises, at least in part, compounds wherein hydrogen is bonded to nitrogen. Preferably such compounds are selected from the group comprising polyamines, polyamides, polyimines and polyolamines, more preferably polyamines. Non-limiting examples of such compounds include primary and secondary amine terminated polyethers. Preferably such polyethers have a molecular weight of greater than about 1500, a functionality of from 2 to 6, and an amine equivalent weight of from about 200 to about 6,000. Such amine terminated polyethers are typically made from an appropriate initiator to which a lower alkylene (e.g. ethylene, propylene, butylene and mixtures thereof) oxide is added with the resulting hydroxyl terminated polyol being subsequently aminated. If two or more alkylene oxides are used, they may be present either as random mixtures or as blocks of one or the other polyether. For ease of amination, it is especially preferred that the hydroxyl groups of the polyol be essentially all secondary hydroxyl groups. Typically, the amination step replaces the majority but not all of the hydroxyl groups of the polyol.

If the foam pieces are polyurethane foam or a urea-modified polyurethane foam, it is possible, and indeed preferred, to use a single polyol or a mixture of polyols which possesses an overall ethylene oxide content in the range of from about 15 to about 80 preferably from about 20 to about 70, more preferably from about 35 to about 70, most preferably from about 50 to about 65, percent by weight, the remainder comprised of other polyoxyalkylene groups such as propylene oxide, butylene oxide or mixtures thereof. While a preferred and practical method of achieving such an overall ethylene oxide content is by blending a hydrophilic polyol and a non-hydrophilic polyol as described hereinabove, it will be appreciated that it is possible and likely even preferred to use a single polyol which possesses substantially the same ethylene oxide content as a mixture of a hydrophilic polyol and a non-hydrophilic polyol. Such a polyol is disclosed in copending U.S. patent application Ser. No. 08/576,695, filed Dec. 21, 1995, the contents of which are hereby incorporated by reference.

As discussed hereinabove, in one embodiment of the present process, the superabsorbent material is incorporated in the foam pieces, preferably pursuant to the teachings of the Wilson applications referred to hereinabove and incorporated herein by reference.

The superabsorbent material can be in any form, such as in the form of particles, flakes or fibers. A discussion of suitable superabsorbent materials may be found in SUPERABSORBENT POLYMERS, Edited by Bucholz et al. (1994), the contents of which are hereby incorporated by reference.

Preferably, the superabsorbent material is a synthetic polymer such as a cellulosic polymer or a polymer of at least one of an acrylic monomer and vinyl monomer, although it is possible to use other materials such as copolymers of maleic acid and isobutylene (typically in fiber form), and polyethers. A non-limiting example of a suitable cellulosic polymer is a carboxymethyl cellulose and alkali metal salts thereof A non-limiting example of a suitable polymer of at least one of an acrylic monomer and vinyl monomer may be selected from the group consisting of polyvinylpyrrolidone, sulfonated polystyrene, polysulfethyl acrylate, poly(2-hydroxyethylacrylate), polyacrylamide, poly(acrylic acid) an alkali metals salts thereof, poly(acrylic acid alkali metal salt), starch modified polyacrylic acid and alkali metal salts thereof poly(starch modified acrylic acid alkali metal salt), hydrolyzed polyacrylonitrile and alkali metal salts thereof, poly (hydrolyzed polyacrylonitrile alkali metal salt), poly (vinyl alcohol acrylic acid alkali metal salt), salts thereof and mixtures thereof. Most preferably, the superabsorbent material is a poly(acrylic acid alkali metal salt) such as poly (sodium acrylate).

While the amount of superabsorbent material incorporated into the foam pieces is not particularly restricted, it is preferred that the superabsorbent material be present in an amount greater than about 20 parts by weight per hundred parts by weight of active hydrogen-containing compound used to produce the foam pieces. More preferably, the superabsorbent material is present in an amount in the range of from about 30 to about 150 parts, even more preferably from about 60 to about 110, most preferably from about 40 to about 90, by weight per hundred parts by weight of active hydrogen-containing compound used to produce the foam pieces. Of course, as improvements are made to superabsorbent materials, it is contemplated that the loading level required in the foam pieces may be reduced while maintaining a given absorption and retention.

The manner by which the uniform mixture of isocyanate, active hydrogen-containing compound and superabsorbent material is prepared is not particularly restricted. Thus, it is possible to preblend the components in a separate tank which is then connected to a suitable mixing device for mixing with the aqueous blowing agent and catalyst. Alternatively, it is possible to preblend the superabsorbent material with the active hydrogen-containing compound. This preblend could then be fed to a suitable mixhead which would also receive independent streams of the isocyanate, the aqueous blowing agent and the catalyst (the aqueous blowing agent and catalyst streams could be combined prior to the mixhead, if desired). In this embodiment, care would have to be taken to design the mixhead to ensure that the preblend and isocyanate streams are adequately mixed at the time that the aqueous blowing agent and catalyst stream(s) are added.

As is known in the art, aqueous blowing agents such as water can be used as a reactive blowing agent in the production of isocyanate-based polymeric foam. Specifically, water reacts with the isocyanate forming carbon dioxide which acts as the effective blowing agent in the final polymeric foam product. Optionally, organic blowing agents may be used in conjunction with the aqueous blowing agent, although the use of such blowing agents is generally being curtailed for environmental considerations. It is known in the art that the amount of water used as a blowing agent in the preparation of an isocyanate-based polymeric foam is conventionally in the range of from about 0.5 to as high as about 20 or more parts by weight, preferably from about 1.0 to about 5.0 parts by weight, based on 100 parts by weight of the total active hydrogen-containing compound content in the reaction mixture. Since the amount of water used in the production of an isocyanate-based polymeric foam is limited by the fixed properties expected in the polymeric foam, it may be necessary, in certain circumstances, to utilize a substantially inert liquid extenders when high loadings of filler material are contemplated. Non-limiting examples of suitable liquid extenders include halogenated hydrocarbons and high molecular weight hydrocarbons.

The catalyst added to the isocyanate, active hydrogen-containing compound and superabsorbent material is a compound capable of catalyzing the polymerization reaction. Such catalysts are known, and the choice and concentration thereof is within the purview of a person skilled in the art. See for example U.S. Pat. Nos. 4,296,213 and 4,518,778, the contents of each of which is incorporated herein by reference. Non-limiting examples of suitable catalysts include tertiary amines and/or organometallic compounds. Additionally, as is known in the art, when the objective is to produce an isocyanurate, a Lewis acid must be used as the catalyst, either alone or in conjunction with other catalysts. Of course it will be understood by those skilled in the art that a combination of two or more catalysts may be suitably used.

As will be clearly understood by those of skill in the art, it is contemplated that conventional additives in the isocyanate-based polymer art be used in the process to produce isocyanate-based polymeric foam pieces. Non-limiting examples of such additives include: surfactants (e.g. organo-silicone compounds available under the tradename L-540 from Osi Specialities, Witco Corporation.), extenders (e.g. halogenated paraffins commercially available as Cereclor S45), cross-linkers (e.g. low molecular weight reactive hydrogen-containing compositions), pigments/dyes, flame retardants (e.g. halogenated organo-phosphoric acid compounds), inhibitors (e.g. weak acids), nucleating agents (e.g. diazo compounds), anti-oxidants, plasticizers/stabilizers (e.g. sulfonated aromatic compounds) and biocides. The amounts of these additives conventionally used would be within the purview of a person skilled in the art.

Once the aqueous blowing agent and catalyst have been added to the uniform mixture of isocyanate, active hydrogen-containing compound and superabsorbent material, a reaction mixture is formed. This reaction mixture is then expanded to produce an isocyanate-based polymeric foam which may then be converted into foam pieces as described hereinabove.

Thus, the foam pieces have a cellular structure. If the foam pieces contain a superabsorbent material, it is preferred that the foam pieces are capable of: (i) absorbing at least about 10 times its weight of a 0.9 wt./wt. % aqueous NaCl solution maintained at a temperature of from about 20° to about 25° C., and (ii) retaining at least about 10 times its weight of aqueous NaCl solution which is bound to the superabsorbent material. Preferably the foam is capable of: (i) absorbing at from about 10 to about 50, more preferably from about 10 to about 30, most preferably from about 10 to about 20, times its weight of a 0.9 wt./wt. % aqueous NaCl solution maintained at a temperature of from about 20° to about 25° C., and (ii) retaining from about 10 to about 50, more preferably from about 10 to about 30, most preferably from about 10 to about 20, times its weight of absorbed 0 9 wt./wt. % aqueous NaCl solution which is bound to the superabsorbent material.

The ability of the isocyanate-based polymeric foam to absorb 0.9 wt./wt. % aqueous NaCl solution (also referred to as "the saline solution") can be assessed by following "tea bag" protocol: (i) weigh empty tea bag ($W_1$); (ii) weigh test sample of isocyanate-based polymeric foam ($W_2$)—the preferred test sample is a disk having a diameter of 2 inches and a thickness of ½ inch, (iii) place test sample inside empty tea bag and seal tea bag, (iv) completely submerge sealed tea bag in the saline solution maintained at a temperature of $22°\pm2°$ C. for a period of 1 hour, (v) removed seal tea bag from saline solution and suspend to allow gravity drainage device for 5 minutes, (vi) weigh sealed tea bag ($W_3$), and (vii) calculate ($W_3-W_1-W_2$)/$W_2$ and report as the amount of 0.9 wt./wt. % aqueous NaCl solution absorbed as a multiple of the weight of the original test sample of isocyanate-based polymeric foam ($W_2$) (another way in which to report the results is as units mass of 0.9 wt./wt. % aqueous NaCl solution absorbed per unit mass of foam).

The ability of the isocyanate-based polymeric foam to absorb 0.9 wt./wt. % aqueous NaCl solution (also referred to as "the saline solution") can be assessed by following protocol: (i) weigh test sample of isocyanate-based polymeric foam ($W_1$), (ii) immerse test sample in saline solution maintained at a temperature of from about 20° to about 25° C. for a period of at least 30 minutes, (iii) remove test sample from saline solution and maintain on drip screen or similar device for 3 minutes, (iv) weigh test sample ($W_f$), and (iv) calculate ($W_f-W_i$)/$W_i$ and report as the amount of saline solution absorbed as a multiple of the weight of the original test sample of isocyanate-based polymeric foam ($W_i$) (another way in which to report the results is as units mass of saline solution absorbed per unit mass of foam). The ability of the foamed isocyanate-based polymer to retain 0.9 wt./wt. % aqueous NaCl solution (also referred to as "the saline solution") can be assessed by conducting the absorption protocol and the following subsequent steps: (v) compress the test sample containing absorbed saline solution until no more saline solution can be forcibly expelled (e.g. at a compressive force of at least about 1.0 psi, more preferably at least about L13 psi) from the test sample, (vi) weigh test sample ($W_r$), and (iv) calculate ($W_r-W_i$)/$W_i$ and report as the amount of saline solution retained as a multiple of the weight of the original test sample of isocyanate-based polymeric foam ($W_i$) (another way in which to report the results is as units mass of saline solution retained per unit mass of foam). Thus, the two protocols distinguish between saline solution which is physically and chemically bound to the foam (i.e. absorbed) and saline solution which only chemically bound to the foam (i.e. retained). For further information, see Chapter 8 (and the references cited therein) of "SUPERABSORBENT POLYMERS Science and Technology", ACS Symposium Series 573, Edited by Bucholz et al. (1994), the contents of which are hereby incorporated by reference.

The foam pieces preferably have a density of from about 1.0 pcf to about 15.0 pcf, more preferably from about 1.0 pcf to about 12.0 pcf even more preferably from about 1.0 pcf to about 8.0 pcf, most preferably from about 1.5 pcf to about 5.0 pcf.

The binder used in Step (i) of the present process comprises an isocyanate and an active hydrogen containing compound. The choice of isocyanate and active hydrogen-containing compound for use in the binder is not particularly restricted. The discussion hereinabove of useful isocyanates and active hydrogen-containing compounds to prepare the foam pieces applies equally to the binder. Preferably, the weight ratio of active hydrogen-containing compound to isocyanate used in the binder is in the range of from about 1:1 to about 3:1 more preferably in the range of from about 1.5:1 to about 2.5;1. The preferred binder for use in Step (i) of the present process comprises an isocyanate and a polyol, more preferably an isocyanate and a non-hydrophilic polyol.

As discussed hereinabove, a preferred aspect of the present process relates to the use isocyanate-based polymeric foam pieces incorporating a superabsorbent material. Alternatively, it is possible to utilize: (i) isocyanate-based polymeric foam pieces which may or may not have incorporated therein a superabsorbent material, in combination with (ii) a superabsorbent material in the binder. The discussion hereinabove of superabsorbent materials incorporated in the foam pieces is equally applicable here. When a superabsorbent material is used in the binder, it is preferred that the superabsorbent material be present in an amount greater than about 20 parts by weight per hundred parts by weight foam pieces. More preferably, the superabsorbent material is present in an amount in the range of from about 30 to about 150 parts, even more preferably from about 60 to about 110, most preferably from about 40 to about 90, by weight per hundred parts by weight foam pieces. Of course, as improvements are made to superabsorbent materials, it is contemplated that the loading level required in the foam pieces may be reduced while maintaining a given absorption and retention.

When a superabsorbent material is used in the binder, it is preferred that Step (i) of the present process comprise mixing the foam pieces and the binder comprising isocyanate and active hydrogen-containing compound, and thereafter adding the superabsorbent material This mode of mixing optimizes production of a mixture with substantially uniform distribution of the binder components (i.e. isocyanate, active hydrogen-containing compound and superabsorbent material) and the foam pieces. Thus, if the superabsorbent material was added to the binder prior to mixing with the foam pieces, the viscosity of the resulting binder would significant hinder handling of the binder and mixing it with the foam pieces. Further, if the superabsorbent material was added to the foam pieces to form a dry mixture, uniformity of the mixture would likely be comprised upon addition of the binder.

The amount of binder used to produce the mixture in Step (i) of the present process should be the minimum required to adequately coat the surface of substantially all of the foam pieces. If too little binder is used, the resulting mixture will be more difficult to handle and the foam pieces will not bond to one another properly resulting in a rebond foam which will likely lack integrity. If too much binder is used, it will impregnate the foam pieces resulting in a poor quality rebond foam product. Preferably, the binder is present in the mixture in an amount in the range of from about 5 to about 25, more preferably from about 5 to about 20, percent by weight per hundred parts by weight isocyanate-based polymeric foam pieces.

Conventional additives used in the rebond foam art may be incorporated in the binder used in the present process. For example, in certain cases, it may be preferred to colour the rebond foam by using a pigment in the binder. Preferably, the pigment is in liquid form and is used in an amount which does not deleteriously affect the viscosity of the binder.

In Step (ii) of the present process, the mixture produced in Step (i) is placed in a mold. In Step (iii) of the present process, the mixture in the mold is compressed. The mold may be of a conventional nature used in the rebond foam art.

In one embodiment, the process is a batch process in which case the mold comprises a bowl for receiving the mixture from Step (i) and a lid which is sealably engageable with the bowl to define a mold cavity. The mold cavity is generally in the shape of a cube although the shape of the mold cavity can be readily modified to suit the application of the product. Further, the lid is adjustable to compress the mixture in the mold to perform Step (iii) of the present process.

In another embodiment, the process is conducted in a semi-continuous or continuous manner using a compression conveyor—see, for example page 13.2 in Herrington et al. referred to above and incorporated herein by reference. The compression conveyor comprises a pair of generally parallel conveyors having an angled opening wherein one of the conveyors is angled away from the other conveyor. Thus, the mixture enters the angled opening wherein it is compress as it is passed to the parallel conveyors which act as the mold.

Steps (iv) and (v) of the present process may be conveniently conducted concurrently. There are a number of embodiments for these Steps of the present process.

In one embodiment, Step (iv) may be conducted at a temperature of at least about 90° C., more preferably at a temperature in the range of from about 95° to about 120° C. In this embodiment, it is not necessary to chemically catalyze the reaction between the isocyanate and the active hydrogen-containing compound in the binder—i.e., the relatively high temperature will promote reaction between the isocyanate and the active hydrogen-containing compound in the binder A preferred means by which to heat the mixture in the mold to the appropriate temperature is to diffuse a hot gas through the mixture. In this instance, it is preferred that the mold be perforated or otherwise adapted to permit diffusion of a hot gas through the contents of the mold cavity. While the nature of the hot gas used to heat the mixture to the appropriate temperature is not particularly restricted (provided, of course, that the hot gas is substantially inert to the components in the mixture), it has been found convenient to use steam to heat the mixture in the mold.

In another embodiment, Step (iv) may be conducted at a relatively low temperature (e.g. from about 50° to about 90° C.). The mold may be designed as discussed in the previous paragraph to facilitate heating of the mixture. If such relatively low temperatures are used in Step (iv) of the present process, it is preferred to utilize a catalyst compound to facilitate reaction of the isocyanate and the active hydrogen-containing compound in the binder. The choice of catalyst is conventional—see, for example, the discussion hereinabove with respect to the production of the foam pieces. Preferably, in this embodiment, the catalyst is incorporated into the binder. The catalyst should be used in an amount which will cure the binder in a reasonable period of time. Preferably, the catalyst is incorporated in an amount less than about 2.0, more preferably in the range of from about 0.5 to about 1.5, parts by weight per hundred parts by weight binder The catalyst may also be in gaseous form in which case, rather than incorporating into the binder, the catalyst may be simply diffused through the mixture.

Preferably, Step (iv) is conducted for a sufficient period of time to ensure proper bonding of the foam pieces (i.e., substantially complete reaction of the isocyanate and the active hydrogen-containing compound in the binder). Thus, if the period of time is insufficient, proper bonding of the foam pieces to one another will likely not occur. Further, if the period time is too long, significant energy will be wasted. Generally, it has been found that a period of from about 5 minutes to about 30 minutes is satisfactory for Step (iv) of the present process.

Step (iv) results in reaction of the isocyanate and the active hydrogen-containing compound in the binder which, in turn results in bonding of the foam pieces to one another to form the rebond foam—i.e., Step (v) of the present process. The rebond foam may be then removed from the mold and allowed to cool and dry (i.e., if steam is used to cure the binder) for a sufficient period of time.

The rebond foam will generally have a density greater than the foam pieces used to produce it. Preferably, the ratio of the density of the rebond foam to the density of the isocyanate-based polymeric foam pieces is in the range of from about 2.0 to about 5.0, more preferably in the range of from about 2.5 to about 4.5.

Embodiments of the present invention will now be described with reference to the following Examples which should not be construed as limiting the scope of the invention. The term "pbw" used in the Examples refers to parts by weight.

In the Examples the following compounds were used:

1. DABCO-T16, a polymerization catalyst commercially available from Air Products and Chemicals, Inc.;
1. Voranol 3010, a non-hydrophilic polyether polyol having a molecular weight of approximately 3000 and an ethylene oxide content of less than about 20% by weight, commercially available from The Dow Chemical Company;
1. TDI 80, a blend of 80% by weight 2,4-toluene diisocyanate, and 20% by weight 2,6-toluene diisocyanate commercially available from Bayer Corporation under the tradename Mondur TD-80 Grade A; and
1. IM4500, starch grafted sodium polyacrylate available from Hoechst Celanese Corporation; and
1. Polyurethane foam pieces: (i) having a particle size of approximately ½', (ii) having a density of about 2.2 pcf, (iii) derived from a polyol blend comprising 70 parts by weight hydrophilic polyol and 30 parts by weight non-hydrophilic polyol, and (iv) containing 45 parts by weight IM4500 per hundred parts by weight polyol blend.

EXAMPLES 1–5

In these Examples, a series of rebond foams were produced using a chemically catalyzed binder and relatively low temperatures.

Thus, 500 g of foam pieces where dispensed in a 5 gallon pail wherein they were mixed with 100 g (i.e., 20 parts by weight per hundred parts by weight foam pieces) of a binder comprising 66⅔ parts by weight Voranol 3010, 33⅓ parts by weight TDI and 1 part by weight DABCO T-16. At this point [SAP], if used, was added to the mixture. Mixing was conducted during addition of the binder and the [SAP], if used, and for a period of 5 minutes after addition of the last component.

The mixture was then transferred to the bowl of a preheated (70° C.), water jacketed mold having the following dimensions: 10"×10"×4". The mixture was manually patted into the mold until all of the mixture was in the bowl. The lid of the mold was closed and engaged the bowl. The mold was maintained in a closed position at the preheat temperature for a period of 30 minutes. The resulting rebond foam was then removed from the mold.

Each rebond foam sample was cut to provide test samples having the following dimensions: 3"×5"×½". The saline solution absorption and retention properties of each of the test samples was assessed using the absorption and retention protocols described above. The results, reported for each test sample as the average absorption and retention, respectively, for four test samples, are provided in Table 1.

For comparison, the foam pieces used to produce the rebond foam of these Examples had an absorption of about 30 and a retention of 12, grams 0.9 wt./wt. % NaCl aqueous solution per gram foam. This demonstrates that the present rebond foam can be made with a very small comprise in retention compared to the original foam pieces used to produce the rebond foam (the difference in absorption is not seen as critical since, in applications such as personal hygiene devices, retention is the more important property).

TABLE 1

| Example | SAP[a] | Density (pcf) | Absorption | Retention |
|---|---|---|---|---|
| 1 | 0 | 7.06 | 11.3 | 8.8 |
| 2 | 5 | 7.17 | 11.4 | 9.1 |
| 3 | 10 | 7.46 | 11.0 | 9.6 |
| 4 | 20 | 8.06 | 11.7 | 9.9 |
| 5 | 30 | 9.13 | 11.7 | 10.7 |

[a]parts by weight per hundred parts by weight foam pieces

EXAMPLE 6

In this Example, a rebond foam was made without a chemical catalyst in the binder and at relatively high temperature.

Thus, 1500 g of foam pieces where dispensed into a conventional cement mixture wherein they were mixed with 150 g (i.e., 10 parts by weight per hundred parts by weight foam pieces) of a binder comprising 66⅔ parts by weight Voranol 3010 and 33⅓ parts by weight TDI. Mixing was conducted during addition of the binder over a period of about 60 minutes.

The mixture was then transferred to the bowl of an unheated, steam jacketed mold having the following fixed dimensions: 24"×24". The lid of the mold was closed, lowered to provide a height of 4" (i.e., the overall dimension of the mold cavity was 24"×24"×4") and engaged to the bowl. The mold was maintained in a closed position with the application of steam for a period of 25 minutes. The resulting rebond foam was then removed from the mold and allowed to dry for 24 hours.

The resulting rebond foam sample was cut to provide four test samples having the following dimensions: 3"×5"×½". The saline solution absorption and retention properties of the test samples was assessed using the absorption and retention protocols described above. The average saline solution absorption for the four test samples was 9.8 grams saline solution per gram foam. The average saline solution retention for the four test samples was 8.5 grams saline solution per gram foam.

For comparison, the foam pieces used to produce the rebond foam of these Examples had an absorption of about 30 and a retention of 12, grams 0.9 wt./wt. % NaCl aqueous solution per gram foam. This demonstrates that the present rebond foam can be made with a very small comprise in retention compared to the original foam pieces used to produce the rebond foam (the difference in absorption is not seen as critical since, in applications such as personal hygiene devices, retention is the more important property).

What is claimed is:

1. A rebond foam comprising a plurality of isocyanate-based polymeric foam pieces bonded to one another with an isocyanate-based binder, a superabsorbent material being comprised in one or both of the isocyanate-based polymeric foam pieces and the isocyanate-based binder, the rebond foam being capable of: (i) absorbing at least about 5 times its weight of a 0.9 wt./wt. % aqueous NaCl solution maintained at a temperature of from about 20° to about 25° C., and (ii) retaining at least about 5 times its weight of absorbed aqueous NaCl solution which is bound to the superabsorbent material.

2. The rebond foam defined in claim 1, wherein the isocyanate-based polymeric foam pieces comprise the superabsorbent material.

3. The rebond foam defined in claim 1, wherein a portion of the isocyanate-based polymeric foam pieces comprise the superabsorbent material.

4. The rebond foam defined in claim 1, wherein substantially all of the isocyanate-based polymeric foam pieces comprise the superabsorbent material.

5. The rebond foam defined in claim 1, wherein the isocyanate-based binder comprises the superabsorbent material.

6. The rebond foam defined in claim 1, wherein both the isocyanate-based polymeric foam pieces and the isocyanate-based binder comprise the superabsorbent material.

7. The rebond foam defined in claim 1, wherein the isocyanate-based polymeric foam pieces comprise polyurethane foam.

8. The rebond foam defined in claim 1, wherein the isocyanate-based polymeric foam pieces have a diameter in the range of from about 0.2 to about 1.0 inches.

9. The rebond foam defined in claim 1, wherein the isocyanate-based polymeric foam pieces have a diameter in the range of from about 0.2 to about 0.8 inches.

10. The rebond foam defined in claim 1, wherein the ratio of the density of the rebond foam to the density of the isocyanate-based polymeric foam pieces is in the range of from about 2.0 to about 5.0.

11. The rebond foam defined in claim 1, wherein the ratio of the density of the rebond foam to the density of the isocyanate-based polymeric foam pieces is in the range of from about 2.5 to about 4.5.

12. The rebond foam defined in claim 1, wherein the isocyanate-based binder is the reaction product an isocyanate and a polyol.

13. The rebond foam defined in claim 1, wherein the isocyanate-based polymeric foam pieces are the reaction product of an isocyanate and a polyol.

14. The rebond foam defined in claim 1, wherein the polyol is derived from a mixtures of oxides comprising ethylene oxide in an amount in the range of from about 15 to about 80 percent by weight and another polyoxyalkylene compound in an amount in the range of from about 20 to about 85 percent by weight.

15. The rebond foam defined in claim 13, wherein the polyol comprises from about 20% to about 90% by weight of a hydrophilic polyol and from about 10% to about 80% by weight of a non-hydrophilic polyol.

16. The rebond foam defined in claim 1, wherein the superabsorbent material is present in the isocyanate-based foam pieces an amount greater than about 30 parts by weight per hundred parts by weight of active hydrogen-containing compound used to produce the isocyanate-based polymeric foam pieces.

17. The rebond foam defined in claim 1, wherein the first superabsorbent material is present in the foam pieces in an amount in the range of from about 30 to about 150 parts by weight per hundred parts by weight of active hydrogen-containing compound used to produce the isocyanate-based polymeric foam pieces.

18. The rebond foam defined in claim 1, wherein superabsorbent material is a synthetic polymer.

19. The rebond foam defined in claim 1, wherein the superabsorbent material is selected from the group consisting of polyvinylpyrrolidone, sulfonated polystyrene, polysulfethyl acrylate, poly(2-hydroxyethylacrylate), polyacrylamide, polyacrylic acid, poly(acrylic acid alkali metal salt), starch modified polyacrylic acid, poly(starch modified acrylic acid alkali metal salt), hydrolyzed polyacrylonitrile, poly(hydrolyzed polyacrylonitrile alkali metal salt) and mixtures thereof.

20. A diaper comprising the rebond foam defined in claim 1.

21. A disposable diaper comprising the rebond foam defined in claim 1.

22. A feminine sanitary napkin comprising the rebond foam defined in claim 1.

* * * * *